(12) United States Patent
Duccini

(10) Patent No.: US 9,005,589 B2
(45) Date of Patent: Apr. 14, 2015

(54) COSMETIC COMPOSITION MADE FROM ION-EXCHANGE RESINS FILLED WITH LIPOAMINOACIDS

(75) Inventor: Yves Duccini, Vielmur/Agout (FR)

(73) Assignee: Societe d'Exploitation de Produits pour les Industries Chimiques Seppic, Paris (FR)

( * ) Notice: Subject to any disclaimer, the term of this patent is extended or adjusted under 35 U.S.C. 154(b) by 80 days.

(21) Appl. No.: 13/380,747

(22) PCT Filed: May 25, 2010

(86) PCT No.: PCT/FR2010/051007
§ 371 (c)(1),
(2), (4) Date: Dec. 23, 2011

(87) PCT Pub. No.: WO2010/149889
PCT Pub. Date: Dec. 29, 2010

(65) Prior Publication Data
US 2012/0093750 A1    Apr. 19, 2012

(30) Foreign Application Priority Data
Jun. 24, 2009   (FR) ..................... 09 54317

(51) Int. Cl.
| | |
|---|---|
| A61K 8/00 | (2006.01) |
| A61K 8/81 | (2006.01) |
| A61K 8/44 | (2006.01) |
| A61K 8/49 | (2006.01) |
| A61Q 19/02 | (2006.01) |
| A61Q 19/06 | (2006.01) |
| A61Q 19/00 | (2006.01) |

(52) U.S. Cl.
CPC ............... *A61K 8/8194* (2013.01); *A61K 8/44* (2013.01); *A61K 8/4913* (2013.01); *A61K 8/8117* (2013.01); *A61K 8/8158* (2013.01); *A61Q 19/02* (2013.01); *A61Q 19/06* (2013.01); *A61Q 19/00* (2013.01)

(58) Field of Classification Search
None
See application file for complete search history.

(56) References Cited

U.S. PATENT DOCUMENTS

| | | | |
|---|---|---|---|
| 2005/0220755 A1* | 10/2005 | Auzerie | 424/78.12 |
| 2006/0024375 A1* | 2/2006 | Hasegawa et al. | 424/489 |
| 2007/0219315 A1 | 9/2007 | Braun | |

FOREIGN PATENT DOCUMENTS

| | | | |
|---|---|---|---|
| EP | 1175914 A2 | 1/2002 | |
| EP | 1250937 A2 | 10/2002 | |
| EP | 1346732 A2 | 9/2003 | |
| EP | 1396265 A1 | 10/2004 | |
| FR | 2668080 A1 | 4/1992 | |
| FR | 2734496 A1 | 11/1996 | |
| FR | 2756195 A1 | 5/1998 | |
| FR | 2762317 A1 | 10/1998 | |
| FR | 2784680 A1 | 4/2000 | |
| FR | 2784904 A1 | 4/2000 | |
| FR | 2790977 A1 | 9/2000 | |
| FR | 2791565 A1 | 10/2000 | |
| FR | 2804432 A1 | 8/2001 | |
| FR | 2807435 A1 | 10/2001 | |
| FR | 2830445 A1 | 4/2003 | |
| FR | 2830774 A1 | 4/2003 | |
| FR | 2852257 A1 | 9/2004 | |
| FR | 2852258 A1 | 9/2004 | |
| FR | 2858554 A1 | 2/2005 | |
| GB | 885087 | 12/1961 | |
| WO | WO 03/061768 | * 7/2003 | A61Q 19/02 |
| WO | 2005040230 A2 | 5/2005 | |

OTHER PUBLICATIONS

Skottner A, et al. 2003. Anti-Inflammatory Potential of Melanocortin Receptor-Directed Drugs. Ann NY Acad Sci.; 994: 84-89.*
International Search Report, dated Aug. 19, 2010, from corresponding PCT application.

* cited by examiner

*Primary Examiner* — Johann R Richter
*Assistant Examiner* — David Browe
(74) *Attorney, Agent, or Firm* — Young & Thompson

(57) ABSTRACT

Disclosed is a composition of ion-exchange resins made from a styrene-divinylbenzene copolymer or an acrylic-divinylbenzene copolymer filled with at least one lipoaminoacid with the formula (I), in which $R_1$ is the chain characterizing a fatty acid, saturated or unsaturated, linear or branching, including 7 to 21 atoms of carbon, $R_2$ is the chain characterizing an amino acid and m is between 1 and 50, or a mixture of the compounds with the formula (I).

20 Claims, No Drawings

COSMETIC COMPOSITION MADE FROM ION-EXCHANGE RESINS FILLED WITH LIPOAMINOACIDS

The present invention relates to compounds based on ion-exchange resins loaded with lipoamino acids, to cosmetic formulations comprising such compositions and also to a process for preparing these compositions.

Many molecules that are biologically active at the surface of the skin are very difficult to formulate in order to prepare cosmetic compositions comprising them, and the development of galenic forms comprising these biologically active molecules poses great problems for the formulator.

Patent application EP11175914A2 discloses a composition of "resinate" which comprises an ion-exchange resin loaded with a pharmaceutically active substance (such as lansoprazole, nifedipine, cisapride or nelfinavir). Patent application EP1396265A1 discloses a pharmaceutical composition which comprises from 5% to 75% of an active ingredient which causes gastrointestinal irritation and from 25% to 95% of an ion-exchange resin, said active ingredient being a polyphosphonic acid.

Patent application EP1346732A2 claims a dosage form which comprises a "resinate" of a hygroscopic active agent, i.e. a hygroscopic agent such as valproic acid, choline salts or pamidronic acid salts, exchanged on an ion-exchange resin.

These patent applications do not disclose topical applications of compositions comprising ion-exchange resins and of biologically active compounds.

It is also very difficult to control the rate of release of these biologically active molecules when they are applied to the skin by means of creams, lotions, gels or emulsions. In general, when such formulations are applied, the biologically active molecules are released in one go. Among the molecules that pose a problem, mention may be made, nonexhaustively, of the following molecules: caffeine used as a slimming molecule and having a lipolytic activity, dimethylethanolamine (or DMEA) used as an antiwrinkle agent, vitamins E and C used as free-radical scavengers, plant, algae and fruit extracts used for their repair and protective properties on the skin and, finally, lipoamino acids used, for example, as skin-lightening active agents, as soothing active agents, or as slimming and lipolytic active agents.

There are all types of difficulties with the galenic formulations of these molecules.

Some molecules are liquid, but insoluble or of low solubility in the cosmetic medium used as a vector, others are pasty at ambient temperature, others crumble at ambient temperature, others are hygroscopic or are destroyed in the presence of light.

A number of these molecules produce a strong, or even unpleasant, odor in the compositions comprising them and it is very difficult for formulators of cosmetics to incorporate them into creams or lotions without the consumer noticing this odor.

Finally, in order to obtain maximum effectiveness, formulators would prefer the active molecules to have a prolonged release on the skin so as to provide a long-lasting activity that is uniform over time. Conversely, they are released immediately upon application of the cosmetic composition, which can be in any form, for instance a gel or a cream, and the amounts released are often too great relative to the desired effect, but their activity is of short duration.

Many solutions, for instance those implementing technologies for encapsulation or for absorption onto an inert support, have been developed by those skilled in the art in order to solve the problems described above.

None is totally satisfactory and especially none simultaneously solves the odor, formulation and controlled-release problems.

Among these solutions, mention may be made of: absorption on porous supports such as silica, zeolites, celluloses and derivatives thereof, polymethyl methacrylates, polymethacrylates or polyacrylates. The major drawbacks of absorption on porous supports are: the small amount of active molecules absorbed, the perception by the consumer of the presence of these porous supports owing to their particle sizes, the impossibility of absorbing certain active agents, and the virtual impossibility of controlling the release of the active molecules. In addition, the odor is often still perceptible. There is also the possibility of implementing technologies for encapsulation by coacervation or complex coacervation, for instance for menthol, for incorporation thereof into toothpastes. In addition to their very high costs, these technologies cannot be used for hydrophilic molecules and the rate of release is abrupt, when the shell of the coacervate ruptures.

The technology of immobilization in wax capsules requires heating the molecules, and their release is conditioned by a rise in temperature or a strong abrasion. In addition, this technology is not suitable for heat-sensitive biological active molecules, which can then degrade and generate the appearance of degradation by-products during the phenomenon of release through a rise in temperature.

Interfacial polymerization techniques involve molecules that are often quite toxic, and are reserved, owing to their cost, for applications with high added value.

Finally, all the technologies based on the thermodynamics of surfactants (such as, for example, liposome or spherulite preparation technologies) are technologies that are difficult to implement, and often not very reliable when it is a question of knowing exactly how many active molecules are protected and how many are free. In addition, their stability over time is very random.

One objective of the present invention is to overcome all or part of the prior art drawbacks noted above.

To this end, the subject of the present invention is a composition (C) of ion-exchange resins based on a styrene/divinylbenzene copolymer or an acrylic/divinylbenzene copolymer loaded with at least one lipoamino acid of formula (I):

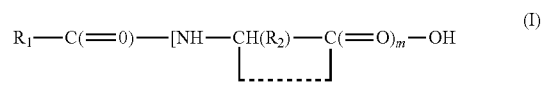

in which $R_1$ represents the characterizing chain of a linear or branched, saturated or unsaturated fatty acid containing from 7 to 21 carbon atoms, $R_2$ represents the characterizing chain of an amino acid and m is between 1 and 50, or a mixture of said compounds of formula (I).

According to one preferred aspect of the invention, the composition (C) defined above is characterized in that said resin contains at least one quaternary ammonium function.

According to one preferred aspect of the invention, the composition (C) defined above is characterized in that said lipoamino acid is chosen from: N-(ω-undecylenoyl)phenylalanine, octanoylglycine, undecylenoyl glycine, palmitoyl proline, dipalmitoyl hydroxyproline, cocoylalanine and palmitoylglycine.

The expression "ion-exchange resin loaded with a lipoamino acid" denotes a resin of which the exchangeable ion is replaced with said lipoamino acid in its saline form.

In formula (I), $R_1$—C(=O)— represents in particular one of the octanoyl, decanoyl, undecylenoyl, dodecanoyl, tetradecanoyl, hexadecanoyl, octadecanoyl, eicosanoyl, docosanoyl, 8-octadecenoyl, eicosenoyl, 13-docosenoyl, 9,12-octadecadienoyl or 9,12,15-octadecatrienoyl radicals.

More particularly, the fragment $R_1$—C(=O) is chosen from octanoyl, ω-undecylenoyl, dodecanoyl, hexadecanoyl, 8-octadecenoyl, 13-docasenoyl, 9,12-octadecadienoyl or 9,12,15-octadecatrienoyl radicals.

For an amino acid represented by general formula (IIIa):

as for a cyclic amino acid represented by formula (IIIb):

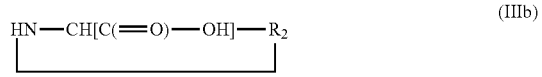

the characterizing chain will be the chain represented by $R_2$.

$R_2$ represents in particular the characterizing chain of an amino acid chosen from glycine, alanine, serine, aspartic acid, glutamic acid, valine, threonine, arginine, lysine, proline, leucine, phenylalanine, isoleucine, histidine, tyrosine, tryptophan, asparagine, glutamine, cysteine, cystine, methionine, hydroxyproline, hydroxylysine, sarcosine or ornithine.

The subject of the invention is principally a composition as defined above, in which said compound of formula (I) as defined above has at least one of the residues

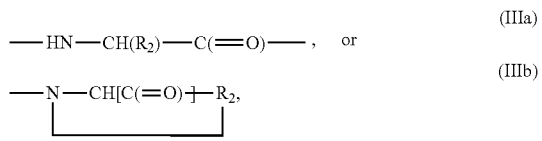

in which $R_2$ represents the characterizing chain of phenylalanine, of tyrosine, of histidine, of methionine, of cysteine or of tryptophan.

The subject of the invention is more particularly a composition comprising a compound of formula (I), as defined above, in which m is a decimal number between 1 and 10 and is preferably less than 5.

According to a quite particular aspect of the present invention, in formula (I) as defined above, m is less than or equal to 2 and more particularly less than or equal to 1.4.

According to another quite particular aspect of the present invention, in formula (I) as defined above, m is equal to 1.

According to another particular variant of the present invention, said composition comprises a mixture of compounds of formula (I) as defined above, and, more particularly, either a mixture of compounds of formulae (I), which formulae all comprise the same fragment $R_1$—C(=O), or a mixture of compounds of formulae (I), in which formulae m is equal to 1 and which formulae all comprise the same fragment

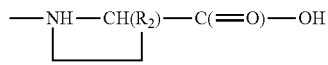

The subject of the present invention is also a cosmetic formulation comprising the composition (C) as defined above, characterized in that the pH of said formulation is between 5 and 7 and the proportion by weight of said composition is less than 1.5% of the total weight.

According to one particular embodiment of the invention, the formulation as defined above is characterized in that the proportion by weight of the composition (C) as defined above is between 0.5% and 0.8% of the total weight.

According to one particular embodiment of the invention, the formulation as defined above is characterized in that it is in the form of a cream gel, an emulsion, a powder, an aqueous dispersion or an oily dispersion.

The subject of the invention is also the use of a formulation as defined above, for cosmetic application to human skin.

The formulation as defined above can also be used as an antiwrinkle agent, while being characterized in that the lipoamino acid used is chosen from: dipalmitoyl hydroxyproline, cocoylalanine and palmitoylglycine.

The formulation as defined above can also be used as a skin-lightening agent or slimming agent, while being characterized in that the lipoamino acid used is chosen from: N-(ω-undecylenoyl)phenylalanine and palmitoyl proline.

The subject of the invention is also a process for preparing a composition (C) as defined above, comprising the step:

a) bringing an ion-exchange resin based on a styrene/divinylbenzene or styrene/acrylic copolymer containing at least one quaternary ammonium into contact with a solution of lipoamino acid of formula (I).

According to one of its characteristics, the process as defined above is characterized in that step a) is a percolation step wherein said solution of lipoamino acid to be loaded passes through a bed of said resin.

Ion-exchange resins are insoluble macromolecules bearing ionic groups which have the property of reversibly exchanging some of their ions, on contact with other ions originating from a different and distinct medium.

These resins have a certain capacity for retaining ions (expressed per gram of dry resin), which corresponds to the number of millimoles (mmol) of ions that the resin can exchange per unit weight of said resin. Ion-exchange resins are also characterized by their particle sizes and by the pK of their functional group.

More particularly, ion-exchange resins, also called anionic resins or basic resins, bear positively charged functional groups and have the property of reversibly exchanging some of their anions associated with the positively charged functional groups, on contact with other anions such as $Cl^-$, $OH^-$, $SO_4^{2-}$, etc., included in the distinct medium then brought into contact with said resin.

In an analogous manner, cation-exchange resins, also called cationic resins or acidic resins, bear negatively charged functional groups and have the property of reversibly exchanging some of their cations associated with the negatively charged functional groups, on contact with other cations such as $Na^+$, $H^+$, $Ca^+$, etc, included in the distinct medium then brought into contact with said resin.

The cationic resins containing monomeric units of styrene and of divinylbenzene or of acrylic derivatives have functional groups bearing sulfonic functions, characterizing strong cationic resins (for example, Amberlite® IRP88, Amberlite® IRP69, Dowex®, etc.), or functional groups bearing carboxylic functions, characterizing weak cationic resins (for example, Amberlite IRP64). In one preferred embodiment, the organic ion-exchange resin is an anionic organic resin which has a styrene/divinyibenzene matrix, such as those sold under the brand Amberlite® 1RA4004

Chloride by the company Rohm & Haas, under the brand Dowex® 2*8 Chloride by the company Dow Chemical Co., under the brand Dowex 1*8 Chloride by the company Dow Chemical Co. and under the brand Dowex 1*2 Chloride by the company Dow Chemical Co.

According to another preferred embodiment, the organic ion-exchange resin is an organic anion-exchange resin comprising monomeric units of acrylic acid derivatives, such as the product sold under the brand Amberlite® IRA67 by the company Rohm & Haas.

According to an even more preferred embodiment, the organic anion-exchange resin is a resin comprising a copolymer containing monomeric units of styrene and of divinylbenzene and comprising quaternary ammonium functions, also called cholestyramine and sold in particular under the brand Duolite® AP143 by the company Rohm & Haas. The exchangeable anion of this resin is the chloride anion.

According to another preferred embodiment, the organic ion-exchange resin is a cationic organic resin comprising a copolymer containing monomeric units of styrene and of divinylbenzene, such as, for example, the resin sold under the brand Amberlite® IRP69, or a resin comprising a copolymer containing monomeric units of acrylic acid and of divinylbenzene, such as, for example, the resin sold under the brand Amberlite® IRP64.

According to another preferred embodiment, an anionic organic resin as described above, for example the Duolite® AP143 resin, is used in combination with an organic cation-exchange resin as described above, for example Amberlite®.

Generally, the composition which is the subject of the invention, comprising compounds of formula (I) and ion-exchange resins, is combined with many types of chemical ingredients normally used in cosmetic formulations, whether they are fatty substances, organic solvents, thickeners, gelling agents, softeners, antioxidants, opacifiers, stabilizers, foaming agents, fragrances, ionic or nonionic emulsifiers, fillers, sequestering agents, chelating agents, preservatives, chemical screening agents or mineral screening agents, essential oils, dyestuffs, pigments, hydrophilic or lipophilic active agents, humectants, for example glycerol, preservatives, dyes, fragrances, cosmetic active agents, mineral or organic sunscreens, mineral fillers such as iron oxides, titanium oxides and talc, synthetic fillers such as crosslinked or non-crosslinked poly(methyl methacrylate)s and nylons, silicone elastomers, sericites or plant extracts, or else lipid vesicles or any other ingredient normally used in the cosmetic industry.

As examples of oils that can be combined with the composition which is the subject of the invention, mention may be made of paraffins, isoparaffins, white mineral oils, vegetable oils, animal oils, synthetic oils, silicone oils and fluoro oils; and more particularly:
  oils of vegetable origin, such as sweet almond oil, coconut oil, castor oil, jojoba oil, olive oil, rapeseed oil, groundnut oil, sunflower oil, wheat germ oil, corn germ oil, soya oil, cottonseed oil, alfalfa oil, poppyseed oil, pumpkin oil, evening primrose oil, millet oil, barley oil, rye oil, safflower oil, candlenut oil, passion flower oil, hazelnut oil, palm oil, shea butter, apricot kernel oil, beauty leaf oil, sysymbrium oil, avocado oil, calendula oil;
  ethoxylated vegetable oils;
  oils of animal origin, such as squalene or squalane;
  mineral oils, such as liquid paraffin, liquid petroleum jelly and isoparaffins;
  synthetic oils, in particular fatty acid esters such as butyl myristate, propyl myristate, cetyl myristate, isopropyl palmitate, butyl stearate, hexadecyl stearate, isopropyl stearate, octyl stearate, isocetyl stearate, dodecyl oleate, hexyl laurate, propylene glycol dicaprylate, esters derived from lanolic acid, such as isopropyl lanolate or isocetyl lanolate, fatty acid monoglycerides, diglycerides and triglycerides, for instance glyceryl triheptanoate, alkyl benzoates, poly-alpha-olefins, polyolefines such as polyisobutene, synthetic isoalkanes, for instance isohexadecane or isododecane, perfluoro oils and silicone oils. Among the latter, mention may more particularly be made of dimethylpolysiloxanes, methylphenylpolysiloxanes, silicones modified with amines, silicones modified with fatty acids, silicones modified with alcohols, silicones modified with alcohols and fatty acids, silicones modified with polyether groups, epoxy-modified silicones, silicones modified with fluoro groups, cyclic silicones and silicones modified with alkyl groups.

As other fatty material that may be combined with the composition which is the subject of the invention, mention may be made of fatty alcohols or fatty acids.

Among the thickening and/or emulsifying polymers that may be combined with the composition which is the subject of the present invention, there are, for example:
  polymers of polyelectrolyte type, for instance copolymers of acrylic acid and of 2-methyl-[(1-oxo-2-propenyl)amino]-1-propanesulfonic acid (AMPS), copolymers of acrylamide and of 2-methyl-[(1-oxo-2-propenyl)amino]-1-propanesulfonic acid, copolymers of 2-methyl-[(1-oxo-2-propenyl)amino]-1-propanesulfonic acid and of (2-hydroxyethyl)acrylate, the homopolymer of 2-methyl-[(1-oxo-2-propenyl)amino]-1-propanesulfonic acid, the homopolymer of acrylic acid, copolymers of acryloylethyltrimethylammonium chloride and of acrylamide, copolymers of AMPS and of vinylpyrrolidone, copolymers of acrylic acid and of alkyl acrylates in which the carbon-based chain contains between ten and thirty carbon atoms, and copolymers of AMPS and of alkyl acrylates in which the carbon-based chain contains between ten and thirty carbon atoms. Such polymers are sold, respectively, under the names SIMULGEL™ EG, SEPIGEL™ 305, SIMULGEL™ NS, SIMULGEL™ 15 800, SIMULGEL™ A, SIMULGEL™ EPG, SIMULGEL™ INS100, SIMULGEL™ FL, SIMULGEL SMS 88, SEPIGEL™ 501, SEPIGEL™ 502, SEPIPLUS™ 250, SEPIPLUS™ 265, SEPIPLUS™ 400, SEPIPLUS S, SEPINOV™ EMT 10, SEPINOV P88 CARBOPOL™, ULTREZ™ 10, ACULYN™ PEMULEN™ TR1, PEMULEN™ TR2, LUVIGEL™ EM, SALCARE™ SC91, SALCARE™ SC92, SALCARE™ SC95, SALCARE™ SC96, FAOCARE™ ET100, FLOCARE™ ET58, HISPAGEL™, NOVEMER™ EC1, ARISTOFLEX™ AVC, ARISTOFLEX™ HBM, RAPITHIX™ A60, RAPITHIX™ A100, COSMEDIA SP and STABILEZE™ 06;
  hydrocolloids of vegetable or biosynthetic origin, for example xanthan gum, karaya gum, carrageenates, alginates and galactomannans;
  silicates; cellulose and derivatives thereof; starch and hydrophilic derivatives thereof; polyurethanes.

Among the waxes that can be used in the context of the present invention, mention may be made, for example, of beeswax; carnauba wax; candelilla wax; ouricury wax; Japan wax; cork fiber wax or sugarcane wax; paraffin waxes; lignite waxes; microcrystalline waxes; lanolin wax; ozokerite; polyethylene wax; hydrogenated oils; silicone waxes; vegetable waxes; fatty alcohols and fatty acids which are solid at ambient temperature; and glycerides which are solid at ambient temperature. Among the emulsifiers that can be combined with the composition which is the subject of the invention, mention may be made, for example, of:

- optionally alkoxylated alkyl polyglycoside fatty esters, and most particularly ethoxylated methyl polyglucoside esters, such as PEG 120 methyl glucose trioleate and PEG 120 methyl glucose dioleate, sold respectively under the names GLUCAMATE™ LT and GLUMATE™ DOE120.
- Alkoxylated fatty esters, such as the PEG 150 pentaerythritol tetrastearate sold under the name CROTHIX™ DS53, and the PEG 55 propylene glycol oleate sold under the name ANTIL™ 141.
- Fatty-chain polyalkylene glycol carbamates, such as the PPG 14 laureth isophoryl dicarbamate sold under the name ELFACOS™ T211, and the PPG 14 palmeth 60 hexyl dicarbamate sold under the name ELFACOS™ GT2125.
- Fatty acids, ethoxylated fatty acids, fatty acid esters of sorbitol, fatty acid esters of mannitol, ethoxylated fatty acid esters, polysorbates, polyglycerol esters, ethoxylated fatty alcohols, sucrose esters, alkyl polyglycosides, sulfated and phosphated fatty alcohols or the mixtures of alkyl polyglycosides and of fatty alcohols described in French patent applications 2 668 080, 2 734 496, 2 756 195, 2 762 317, 2 784 680, 2 784 904, 2 791 565, 2 790 977, 2 807 435, 2 804 432, 2 830 774 and 2 830 445, combinations of emulsifying surfactants chosen from alkyl polyglycosides, combinations of alkyl polyglycosides and of fatty alcohols, polyglycerol or polyglycol or polyol esters, such as the polyglycol or polyglycerol polyhydroxystearates used in French patent applications 2 852 257, 2 858 554, 2 820 316 and 2 852 258.

As examples of opacifying and/or pearlescent agents that may be combined with the composition which is the subject of the present invention, mention may be made of sodium palmitates or stearates or hydroxystearates, magnesium palmitates or stearates or hydroxystearates, ethylene glycol monostearates or distearates or polyethylene glycol monostearates or distearates, copolymer alcohols sold under the name MONTOPOL™ OP1 by the company SEPPIC.

As examples of active ingredients that may be combined with the composition which is the subject of the invention, in order to potentiate by synergy the properties thereof, mention may be made of: compounds having a lightening or depigmenting action, such as, for example, arbutin, kojic acid, hydroquinone, ellagic acid, vitamin C or vitamin C derivatives, for instance magnesium ascorbyl phosphate, polyphenol extracts, grape extracts, pine extracts, wine extracts, olive extracts, marc extracts, apple juice extracts, amino acid derivatives, for instance the undecelenoyl phenylalanine sold under the name SEPIWHITE MSH, peptides; total protein hydrolyzates; partial protein hydrolyzates; polyols (for instance glycerol and butylene glycol); urea; pyrrolidonecarboxylic acid or derivatives of this acid; glycyrrhetinic acid; alpha-bisabolol; sugars or sugar derivatives; polysaccharides or derivatives thereof; hydroxy acids, for instance lactic acid; vitamins or vitamin derivatives, for instance retinol, vitamin E and its derivatives; mineral salts; enzymes; coenzymes, for instance coenzyme Q10; hormones or "hormone-like" compounds, for instance PHYTO-20 AGE™; soya extracts, for instance Raffermine™; wheat extracts, for instance Tensine™ or Gliadine™; plant extracts such as tannin-rich extracts, isoflavone-rich extracts or terpene-rich extracts; freshwater algae extracts or marine algae extracts; marine plant extracts; essential waxes; bacterial extracts; lipids in general and more particularly lipids such as ceramides or phospholipids; active agents having an antimicrobial activity or a purifying action with respect to oily skin; active agents having an energizing or stimulating property, such as SEPITONIC™ M3 or Physiogenyl™; panthenol and derivatives thereof, such as SEPICAP™ MP; anti-aging active agents, such as SEPIVINOL™, SEPIVITAL™, EXTRAMEL™ C or MANOLIVA™; moisturizing active agents such as AQUAXYL™; "anti-photoaging" active agents; active agents which have an immediate tensioning or smoothing action on the skin, for instance SESAFLASH™; active agents that protect the integrity of the dermal-epidermal junction, such as PHYTO-AGE™; active agents which increase extracellular matrix components synthesis, such as SEPITONIC™ M3 or AQUAXYL™; active agents which have a slimming, firming or draining activity, for instance caffeine, caffeine derivatives, theophylline, cyclic adenosine monophosphate (cAMP), ADIPOLESS™, green tea, sage, ginko biloba, ivy, horse chestnut, bamboo, ruscus, butcher's broom, Centella asiatica, heather, meadowsweet, fucus, rosemary, willow, parsnip extracts or potentilla extracts; active agents which create a feeling of "heating" on the skin, such as activators of skin microcirculation, for instance nicotinates; active agents which create a feeling of "coolness" on the skin, for instance menthol and derivatives thereof; active agents which exhibit an action with respect to stem cells; active agents which exhibit an action on the epidermis, the dermis, the hypodermis and the skin appendages (hairs, nails, sebaceous glands, pores, etc.); active agents which exhibit an action with respect to the skin flora.

As sunscreens that may be incorporated into the composition according to the invention, mention may be made of those appearing in the cosmetics directive 76/768/EEC, amended, annex VII.

When the cosmetic formulation which is the subject of the invention is in the form of a cream gel, said formulation comprises: a resin as defined above, a thickener, an oily phase, an active lipoamino acid and water. When the cosmetic formulation which is the subject of the invention is in the form of an emulsion, said formulation comprises: a resin as defined above, a thickener, an oily phase, an active lipoamino acid, at least one surfactant and water.

All the formulations of the present invention are stable when their pH is between 5 and 7. In addition, when the amount of resin does not exceed 1% of the total weight, there is no odor or viscosity problem.

The advantage of the solution of the present invention is that this technology of trapping compounds of formula (I) on ion-exchange resins makes it possible to provide the molecules of compounds of formula (I), which are initially in the form of liquids and/or of pastes, in the form of a fine powder which is non-tacky and very easy to handle. Owing to the selected particle sizes of the resins having a diameter less than or equal to 120 micrometers, the consumer will not perceive the presence of solid particles in the cosmetic formulation comprising the compounds of formula (I) trapped on the ion-exchange resin. There is therefore an undeniable galenic advantage since, once immobilized on an ion-exchange resin, the active molecule may be incorporated into an emulsion, a cream, a gel, a paste or even powders. This will be possible irrespective of the initial form of the molecule. All that is required is for the active molecule to be introduced in liquid form, either by diluting it, or by melting it in any liquid, whether aqueous, alcoholic or hydrotropic.

The mechanism of immobilization of the molecule on the ion-exchange resin, like the mechanism of its release, are controlled by ionic equilibria of chemical reactions. The release of the active molecules can therefore be controlled by varying the nature of the support resin or the manner in which this resin is loaded. This is very difficult with certain forms of protection such as absorption on a support, and completely impossible with technologies such as coacervation.

The size of the particles of an ion-exchange resin is much greater than the size of the pores of the skin. Therefore, the polymeric support which transports the active molecules cannot penetrate under the skin. This is a guarantee of the innocuousness of the technology for the user.

The molecules to which the present invention relates are, inter alia, antiwrinkle, slimming, propigmenting, depigmenting, lightening, emollient, soothing, moisturizing, free-radical scavenging, anti-acne and softening molecules for the skin.

The process which is the subject of the present invention consists in bringing the selected resin into contact with an aqueous or alcoholic solution, or a solution in a solvent, of the molecule that it is desired to trap.

This bringing into contact can be carried out by sparging the resin in the solution to be loaded, and then filtering and rinsing in order to recover the loaded resin. However, charging of the resin by percolation, in which the solution to be loaded will pass through a bed of resin, will be preferred.

By adjusting the concentration of the solution of active material, the contacting time and the nature of the resin, it will then be possible to vary the rate of release of the active molecule when the resinate (or the composition based on resin and on compounds of formula (I)) is brought into contact with the skin.

This release will take place by ion exchange between the loaded resin and either the cations ($Na^+$, $K^+$, $Ca^+$, $H^+$) or the anions ($Cl^-$, $OH^-$) present at the surface of the skin or in the sweat.

The rate of release of the active molecules can also be controlled by mixing loaded resins and nonloaded resins into the cosmetic formulation under consideration. In this case, the release of the active molecule and its action at the surface of the skin will be competing with the trapping on a non-loaded resin. The total release of the active molecules will therefore be decreased and prolonged.

EXAMPLES

1) Preparation of a Composition (A) Based on N-(ω-Undecylenoyl)Phenylalanine and on an Ion-Exchange Resin N-(ω-Undecylenoyl)phenylalanine is a lipoamino acid of molecular formula $C_{20}H_{22}NO_2$, sold by the company SEPPIC under the trade name SEPIWHITE™ MSH, and which has a molecular weight of 331 g/mol.

The theoretical capacity of the ion-exchange resin (Duolite AP 143/1073) is 1.4 grams of N-(ω-undecylenoyl)phenylalanine per gram of resin. A solution of 10 liters comprising a proportion by weight of 1% of N-(ω-undecylenoyl)phenylalanine salified in the form of a sodium salt is buffered at pH 7.5 and stirred for two hours in the presence of 50 grams of Duolite AP 143/1073 by means of a mechanical stirrer in a reactor equipped with a jacket for the circulation of a heat-transfer fluid.

The resulting mixture is then filtered through a cellulose support of which the pore diameter is 25 micrometers. The solid retained on such a filtering support is then washed by successive addition of two solutions of 2 liters of deionized water.

The N-(ω-undecylenoyl)phenylalanine not grafted onto the resin and included in the above filtrate is assayed using an HPLC (High Performance Liquid Chromatography) method.

The assaying of N-(ω-undecylenoyl)phenylalanine in the filtrate, using an HPLC (High Performance Liquid Chromatography) method, indicates an amount of 35 grams of N-(ω-undecylenoyl)phenylalanine, thus meaning that 65 grams of N-(ω-undecylenoyl)phenylalanine were retained on the ion-exchange resin, i.e., for a theoretical amount of resin of 70 grams and for an initial amount of 100 grams of N-(ω-undecylenoyl)phenylalanine included in the solution of 10 liters, a degree of grafting, by weight, of 92% of the N-(ω-undecylenoyl)phenylalanine onto the resin.

After drying, 109.3 grams of a composition (A) comprising 56.5% by weight of N-(ω-undecylenoyl)phenylalanine are obtained.

2) Preparation of a Cream Gel and of an Emulsion Comprising the Composition (A)

A cream gel and an emulsion were prepared at various percentages of Duolite® AP143/1073, at 2 different pHs.

2.1 Preparation of a Cream Gel:

a) A series of cream gels, of which the compositions of ingredients, by weight, are indicated in table 1 below, is prepared:

TABLE 1

| cream gel compositions CG1 to CG4 | | | | |
|---|---|---|---|---|
| | CG1 | CG2 | CG3 | CG4 |
| Oily phase: C8-C10 triglyceride | 3% | 3% | 3% | 3% |
| Polyelectrolyte polymer SEPIPLUS 400[1] | 3% | 3% | 3% | 3% |
| Aqueous phase | | | | |
| Water | Qs 100% | Qs 100% | Qs 100% | Qs 100% |
| Triethanolamine at 99% | Qs pH = 5 | Qs pH = 5 | Qs pH = 5 | Qs pH = 5 |
| Sepicide ™ HB[2] | 1% | 1% | 1% | 1% |
| Composition (A) | 0.5% | 0.8% | 1.0% | 0% |
| SEPIWHITE ™ MSH[3] | 0% | 0% | 0% | 0.28% |

[1]SEPIPLUS ™ 400 is a self-invertible inverse latex of copolymers, such as those described in international publication WO 2005/040230 (INCI name: Polyacrylate-13 & Polyisobutene & Polysorbate 20): sold by the company SEPPIC.
[2]SEPICIDE ™ HB is a mixture of phenoxyethanol, methylparaben, ethylparaben, propylparaben and butylparaben, and is a preservative sold by the company SEPPIC.
[3]SEPIWHITE ™ MSH is the N-(ω-undecylenoyl) phenylalanine sold by the company SEPPIC as a skin-lightening agent.

The cream gels, of which the composition is indicated in table 1 above, are prepared by carrying out the following process:

step a): the polyelectrolyte polymer is dispersed at ambient temperature in water introduced beforehand into a 2 liter beaker, and subjected to mechanical stirring for a period of 15 minutes, by means of a stirrer fitted with an "anchor"-type spindle, at a speed of 80 rpm, so as to form a homogeneous gel;

step b): the oily phase, the composition (A) according to the invention or the SEPIWHITE™ MSH, and the preservative SEPICIDE™ HB, are then added to the gel formed during step a), and the resulting mixture is subjected to stirring by means of a rotor-stator emulsifying device, sold by the company SILVERSON, for a period of 5 minutes at a speed of 3000 rpm at a temperature of 25° C. The pH is then adjusted to a value of 5 by adding 99% triethanolamine.

b) Evaluation of the Properties of the Cream Gels Prepared.

The amount of the cream gels, as prepared above, is then divided into two equal portions in different beakers, which are then placed in a climate-controlled chamber at a temperature regulated at 45° C. The experimenter then examines the appearance of the cream gels present in each climate-controlled chamber at different durations. The observations noted are included in the table below:

TABLE 2 change in appearance of the cream gels CG1 to CG4 during storage at 20° C. and at 45° C.

|  | CG1 | CG2 | CG3 | CG4 |
|---|---|---|---|---|
| Appearance after 7 days at 20° C. | Homogeneous | Homogeneous | Homogeneous | Heterogeneous, presence of grains |
| Appearance after 3 months at 20° C. | Homogeneous | Homogeneous | Homogenous | Heterogeneous, presence of grains |
| Appearance after 3 months at 45° C. | Homogeneous | Homogeneous | Homogeneous | Heterogeneous, presence of grains |

The results obtained in table 2 above show that the composition (A) according to the invention, comprising 56.5% by weight of N-(ω-undecylenoyl)phenylalanine attached to the ion-exchange resin Duolite AP 143/1073, makes it possible to prepare cream gels CG1, CG2 and CG3, comprising respectively 0.28% by weight of N-(ω-undecylenoyl)phenylalanine, 0.45% by weight of N-(ω-undecylenoyl)phenylalanine and 0.56% by mass of N-(ω-undecylenoyl)phenylalanine, which are homogeneous after storage at 20° C. and at 45° C. for a minimum period of 3 months, whereas the cream gel CG4 comprising 0.28% by weight of N-(ω-undecylenoyl) phenylalanine, prepared under the same conditions and according to the same process, shows a heterogeneous appearance after a period of storage of 7 days at 20° C., which is characterized by the presence of grains. The cream gels CG1, CG2 and CG3 also provide the consumer with a persistent sensation of softness when they are applied to the skin.

2.2 Preparation of an Oil-in-Water Emulsion:

a) A Series of Oil-in-Water Emulsions, of which the Compositions of Ingredients, by Weight, are Indicated in Table 3 Below, is Prepared:

TABLE 3 compositions of the oil-in-water emulsions EM1 to EM4

|  | EM1 | EM2 | EM3 | EM4 |
|---|---|---|---|---|
| Oily phase: C8-C10 triglyceride | 10% | 10% | 10% | 10% |
| Polyelectrolyte polymer SEPIPLUS 400[1] | 0.7% | 0.7% | 0.7% | 0.7% |
| Emulsifying system |  |  |  |  |
| MONTANOV 68[4] | 2.5% | 2.5% | 2.5% | 2.5% |
| MONTANOV 202[5] | 2.5% | 2.5% | 2.5% | 2.5% |
| Aqueous phase |  |  |  |  |
| Water | Qs 100% | Qs 100% | Qs 100% | Qs 100% |
| Triethanolamine at 99% | Qs pH = 5 | Qs pH = 5 | Qs pH = 5 | Qs pH = 5 |
| Sepicidem ™ HB[2] | 1% | 1% | 1% | 1% |
| Composition A | 0.5% | 0.8% | 1.0% | 0% |
| SEPIWHITE ™ MSH[3] | 0% | 0% | 0% | 0.28% |

[4]MONTANOV ™ 68 (cetearyl alcohol and cetearyl glucoside) is a self-emulsifable composition sold by the company SEPPIC.
[5]MONTANOV ™ 202 (arachidyl alcohol, behenyl alcohol and arachidyl glucoside) is a self-emulsifable composition such as those described in EP 0977626, sold by the company SEPPIC.

The emulsions, of which the composition is indicated in table 3 above, are prepared by carrying out the following process:

step a): the oily phase and the emulsifying system are introduced successively into a 2 liter beaker, at a temperature of 75° C., and are subjected to mechanical stirring for a period of 15 minutes, by means of a stirrer fitted with an "anchor"-type spindle, at a speed of 80 rpm at a temperature of 75° C., so as to form a homogeneous mixture;

step b): the polyelectrolyte polymer is added to the mixture obtained at the end of step a) at a temperature of 75° C., along with the water. The resulting mixture is subjected to stirring by means of a rotor-stator emulsifying device, sold by the company SILVERSON, for a period of 4 minutes at a speed of 3000 rpm at a temperature of 75° C.;

step c): the mixture obtained at the end of step b) is cooled to a temperature of 30° C. over the course of a period of 10 minutes, and kept stirring during the cooling period by means of a mechanical stirrer fitted with an "anchor"-type spindle, at a speed of 80 rpm.

step d): the composition (A) according to the invention or the SEPIWHITE™ MSH, and the preservative SEPICIDE™ HB, are then added to the mixture resulting from step c) at a temperature of 30° C. The pH is then adjusted to a value of 5 by adding 99% triethanolamine.

b) Evaluation of the Properties of the Emulsions Prepared:

The amount of each emulsion is then divided into two equal portions in different beakers, which are then placed in a climate-controlled chamber at a temperature regulated at 20° C. and in a climate-controlled chamber at a temperature regulated at 45° C. The experimenter then examines the appearance of the emulsions present in each climate-controlled chamber at different durations. The observations noted are included in table 4 below:

TABLE 4 change in appearance of the oil-in-water emulsions EM1 to EM4 during storage at 20° C. and at 45° C.

|  | EM1 | EM2 | EM3 | EM4 |
|---|---|---|---|---|
| Appearance after 48 hours at 20° C. | Homogeneous | Homogeneous | Homogeneous | Heterogeneous, presence of grains |
| Appearance after 3 months at 20° C. | Homogeneous | Homogeneous | Homogeneous | Heterogeneous, presence of grains |
| Appearance after 3 months at 45° C. | Homogeneous | Homogeneous | Homogeneous | Heterogeneous, presence of grains |

The results obtained in table 4 above show that the composition (A) according to the invention, comprising 56.5% by weight of N-(ω-undecylenoyl)phenylalanine attached to the ion-exchange resin Duolite AP 143/1073, makes it possible to prepare oil-in-water emulsions EM1, EM2 and EM3, comprising respectively 0.28% by weight of N-(ω-undecylenoyl)phenylalanine, 0.45% by weight of N-(ω-undecylenoyl)phenylalanine and 0.56% by weight of N-(ω-undecylenoyl)phenylalanine, which are homogeneous after storage at 20° C. and at 45° C. for a minimum period of 3 months, whereas the emulsion EM4 comprising 0.28% by weight of N-(ω-undecylenoyl)phenylalanine, prepared under the same conditions and according to the same process, shows a heterogeneous appearance after a period of storage of 48 hours at 20° C., which is characterized by the presence of grains. The emulsions EM1, EM2 and EM3 also provide the consumer with a persistent feeling of softness when they are applied to the skin.

Cosmetic Formulation Examples

Example 3

Lightening Care Emulsion for Mature Skin

| | |
|---|---|
| MONTANOV ™ 202 | 02.00% |
| MONTANOV ™ 68 | 02.00% |
| Caprylic capric triglycerides | 10.00% |
| Squalane | 10.00 c/o |
| Water | QS 100% |
| Composition A | 0.54% |
| SEPIGEL ™ 305 | 00.70% |
| Magnesium ascorbyl phosphate | 02.00% |
| SEPICIDE ™ HB | 00.30% |
| SEPICIDE ™ CI | 00.20% |
| Fragrance | 00.50% |

Example: 4

Lightening Firming Care Emulsion

| | |
|---|---|
| MONTANOV ™ 202 | 03.00% |
| 24% sodium hydroxide | 00.06% |
| Ethylhexyl methoxycinnamate | 06.00% |
| LANOL ™ 1688 | 08.00% |
| Benzophenone-3 | 04.00% |
| Water | QS 100% |
| Composition A | 0.87% |
| SIMULGEL ™ NS | 00.50% |
| Sepilift ™ DPHP | 00.50% |
| Dimethicone | 02.00% |
| Cyclomethicone | 02.00% |
| Arbutin | 0.3% |
| SEPICIDE ™ HB | 00.30% |
| SEPICIDE ™ CI | 00.20% |
| Fragrance | 00.10% |

Example 5

Lightening Cream Gel Containing Alpha-Hydroxy Acids

| | |
|---|---|
| Hydroxyethylcellulose | 00.80% |
| Ethylhexyl octanoate | 05.00% |
| 60% Sodium lactate | 14.00% |
| Water | QS 100% |
| Composition A | 1.0% |

| | |
|---|---|
| SEPIGEL ™ 305 | 04.20% |
| SEPICIDE ™ HB | 02.00% |
| SEPICIDE ™ Ci | 03.00% |
| Fragrance | 00.10% |

Example 6

Lightening Care Emulsion

| | |
|---|---|
| MONTANOV ™ L | 01.00% |
| Cetyl alcohol | 02.00% |
| Isodecyl neopentanoate | 12.00% |
| Cetearyl octanoate | 10.00% |
| Glycerol | 03.00% |
| Water | QS 100% |
| Composition A | 0.54% |
| SIMULGEL ™ EG | 02.00% |
| Kojic acid | 01.00% |
| SEPICIDE ™ HB | 00.30% |
| SEPICIDE ™ CI | 00.20% |
| Fragrance | 00.10% |

Example 7

Lightening Lotion

| | |
|---|---|
| ORAMIX ™ CG110 | 05.00% |
| KATHON ™ CG | 00.08% |
| Water | QS 100% |
| Composition A | 0.54% |
| Fragrance | 00.10% |

This lotion may be sold in bottles or impregnated into wipes.

The definitions of the commercial products used in the examples are the following:

SEPILIFT™ DHP (INCI name: dipalmitoyl hydroxyproline), sold by the company SEPPIC.

SEPICIDE™ HB is a preserving mixture comprising phenoxyethanol, methylparaben, ethylparaben, propylparaben and butylparaben, sold by the company SEPPIC.

SEPICIDE™ CI is imidazolidinylurea, sold by the company SEPPIC.

SEPICALM™ VG (INCI name: sodium palmitoyl proline and extract of water lily flower), sold by the company SEPPIC.

KATHON™ CG (INCI name: methylisothiazolinone/methyl-chloroisothiazolinone).

SIMULGEL™ EG is a copolymer inverse latex (INCI name: sodium acrylate/sodium acryloyldimethyltaurate copolymer and isohexadecane and Polysorbate 80) sold by the company SEPPIC.

SIMULGEL™ NS is a copolymer inverse latex (INCI name: hydroxyethyl acrylate/sodium acryloyldimethyltaurate copolymer and squalane and Polysorbate 60) sold by the company SEPPIC.

LANOL™ 1688 is cetearyl ethylhexanoate, sold by the company SEPPIC.

SEPIGEL™ 305 is a polymer inverse latex (INCI name: polyacrylamide and C13-C14 isoparaffin and laureth 7).

MONTANOV™ L is an emulsifier based on C14-C22 alcohol and on C12-C20 alkyl polyglycoside.

MONTANOV™ 68 is an emulsifier based on cetearyl alcohol and cetearyl polyglucoside.

MONTANOV™ 202 is an emulsifier based on arachidyl alcohol, behenyl alcohol and arachidyl polyglucoside.

Observation: depending on the exchange capacity of the resin with respect to the lipoamino acids, the amount of resin to be used is about 0.5% so as to have 1% of lipoamino acid in the final formulation, hence the concentrations tested in the formula schemes above.

The invention claimed is:

1. A composition of ion-exchange resins comprising a styrene/divinylbenzene copolymer or an acrylic/divinylbenzene copolymer loaded with at least one lipoamino acid of formula (I):

$$R_1\text{—}C(\!\!=\!\!O)\text{-[at least one amino acid residue]}_m\text{-OH} \quad (I)$$

in which $R_1$—C(=)— represents a linear or branched, saturated or unsaturated fatty acid alkanoyl or alkenoyl radical, $R_1$ containing from 7 to 21 carbon atoms, said at least one amino acid residue according to Formula (IIIa) or Formula (IIIb):

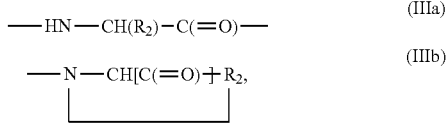

$R_2$ represents a structure completing the amino acid residue of formula IIIb or IIIa and m is between 1 and 50, or a mixture of lipoamino acids of formula (I).

2. The composition as claimed in claim 1, wherein said ion-exchange resins contain at least one quaternary ammonium function.

3. The composition as claimed in claim 1, wherein said lipoamino acid is selected from the group consisting of: N-(ω-undecylenoyl)phenylalanine, octanoylglycine, undecylenoyl glycine, palmitoyl proline, dipalmitoyl hydroxyproline, cocoylalanine and palmitoylglycine.

4. A cosmetic formulation comprising the composition as defined in claim 1, characterized in that the pH of said formulation is between 5 and 7 and the proportion by weight of said composition is less than 1.5% of the total weight.

5. The formulation as claimed in claim 4, characterized in that the proportion by weight of the composition is between 0.5% and 0.8% of the total weight.

6. The composition as claimed in claim 1, wherein said composition is in the form of a cream gel, an emulsion, a powder, an aqueous dispersion or an oily dispersion.

7. A method of cosmetic treatment of human skin comprising a step of applying an effective amount of a formulation as defined in claim 4.

8. A method of treatment of human skin comprising a step of applying an effective amount of a formulation as defined in claim 4, as an antiwrinkle agent, wherein the lipoamino acid used is chosen from: dipalmitoyl hydroxyproline, cocoylalanine and palmitoylglycine.

9. A method of treating skin comprising a step of applying an effective amount of a formulation as defined in claim 4, as a skin-lightening agent or slimming agent, wherein the lipoamino acid used is chosen from: N-(ω-undecylenoyl) phenylalanine and palmitoyl proline.

10. A process for preparing a composition as defined in claim 1, comprising the step:
   a) bringing an ion-exchange resin based on a styrene/divinylbenzene or styrene/acrylic copolymer containing at least one quaternary ammonium into contact with a solution of lipoamino acid of formula (I).

11. The process as claimed in claim 10, characterized in that step a) is a percolation step wherein said solution of lipoamino acid to be loaded passes through a bed of said resin.

12. The composition as claimed in claim 2, said lipoamino acid is selected from the group consisting of: N-(ω-undecylenoyl)phenylalanine, octanoylglycine, undecylenoyl glycine, palmitoyl proline, dipalmitoyl hydroxyproline, cocoylalanine and palmitoylglycine.

13. A cosmetic formulation comprising the composition as defined in claim 2, characterized in that the pH of said formulation is between 5 and 7 and the proportion by weight of said composition is less than 1.5% of the total weight.

14. A cosmetic formulation comprising the composition as defined in claim 3, characterized in that the pH of said formulation is between 5 and 7 and the proportion by weight of said composition is less than 1.5% of the total weight.

15. The composition as claimed in claim 2, wherein said composition is in the form of a cream gel, an emulsion, a powder, an aqueous dispersion or an oily dispersion.

16. The composition as claimed in claim 3, wherein said composition is in the form of a cream gel, an emulsion, a powder, an aqueous dispersion or an oily dispersion.

17. The formulation as claimed in claim 4, characterized in that it is in the form of a cream gel, an emulsion, a powder, an aqueous dispersion or an oily dispersion.

18. The formulation as claimed in claim 5, characterized in that it is in the form of a cream gel, an emulsion, a powder, an aqueous dispersion or an oily dispersion.

19. A method of cosmetic treatment of human skin comprising a step of applying an effective amount of a formulation as defined in claim 5.

20. A method of cosmetic treatment of human skin comprising a step of applying an effective amount of a formulation as defined in claim 6.

* * * * *